(12) United States Patent
Shim

(10) Patent No.: US 12,157,122 B2
(45) Date of Patent: Dec. 3, 2024

(54) MICROFLUIDIC CONNECTION DEVICE

(71) Applicant: KWANGWOON UNIVERSITY INDUSTRY-ACADEMIC COLLABORATION FOUNDATION, Seoul (KR)

(72) Inventor: Joon Sub Shim, Yongin-si (KR)

( * ) Notice: Subject to any disclaimer, the term of this patent is extended or adjusted under 35 U.S.C. 154(b) by 756 days.

(21) Appl. No.: 17/298,061

(22) PCT Filed: Oct. 2, 2019

(86) PCT No.: PCT/KR2019/012926
§ 371 (c)(1),
(2) Date: May 28, 2021

(87) PCT Pub. No.: WO2020/116763
PCT Pub. Date: Jun. 11, 2020

(65) Prior Publication Data
US 2022/0118449 A1 Apr. 21, 2022

(30) Foreign Application Priority Data

Dec. 3, 2018 (KR) .................. 10-2018-0153517

(51) Int. Cl.
*B01L 3/00* (2006.01)
(52) U.S. Cl.
CPC . *B01L 3/502738* (2013.01); *B01L 2200/0689* (2013.01); *B01L 2200/12* (2013.01);
(Continued)

(58) Field of Classification Search
None
See application file for complete search history.

(56) References Cited

U.S. PATENT DOCUMENTS 5,095,938 A * 3/1992 Garrison .............. B01J 19/0046
137/510
11,890,620 B2 * 2/2024 McFarland ....... B01L 3/502715
(Continued)

FOREIGN PATENT DOCUMENTS

EP           2479466 A1    7/2012
KR    10-2014-0110925 A    9/2014
(Continued)

OTHER PUBLICATIONS

International Search Report for PCT/KR2019/012926 mailed on Sep. 17, 2020.

*Primary Examiner* — Brian R Gordon

(57) ABSTRACT

The present invention relates to a microfluidic connection device for enabling faster observation of reactions even with only sample amount far less than that of reaction experiments in which a 96-well particularly used for a conventional sample reaction is used. The objective of the present invention is to provide the microfluidic connection device comprising: a microtube having a fine tube shape; a microvalve comprising a fluid moving unit for causing samples filled in the microtube to flow or stop; a plate-shaped plate; a reaction zone in which chemical reactions between samples supplied through the microtube occur, which has an observation window through which chemical reactions are observed, and which is provided on the upper surface of the plate; a supply tube for connecting the reaction zone with the microtube; and a reaction plate comprising a discharge tube for discharging reactants from the reaction zone.

7 Claims, 17 Drawing Sheets

(52) U.S. Cl.
CPC ... *B01L 2200/16* (2013.01); *B01L 2300/0829* (2013.01); *B01L 2300/087* (2013.01); *B01L 2400/049* (2013.01); *B01L 2400/06* (2013.01)

(56) References Cited

U.S. PATENT DOCUMENTS

| | | | |
|---|---|---|---|
| 2003/0026740 A1* | 2/2003 | Staats | H01J 49/04 |
| | | | 422/503 |
| 2004/0166504 A1 | 8/2004 | Rossier | |
| 2007/0036679 A1 | 2/2007 | Munenaka | |
| 2007/0048194 A1* | 3/2007 | Schulein | B01L 3/565 |
| | | | 422/400 |
| 2008/0057274 A1* | 3/2008 | Hagiwara | F16K 99/0001 |
| | | | 216/49 |
| 2008/0160602 A1 | 7/2008 | He | |
| 2008/0213755 A1* | 9/2008 | Geiser | B01L 3/502723 |
| | | | 435/6.12 |
| 2008/0233018 A1 | 9/2008 | van Dam | |
| 2010/0112723 A1* | 5/2010 | Battrell | G01N 33/53 |
| | | | 422/68.1 |
| 2011/0286885 A1* | 11/2011 | Park | F16K 99/0001 |
| | | | 216/33 |
| 2011/0305607 A1* | 12/2011 | Jung | B01L 3/502738 |
| | | | 422/502 |
| 2018/0257072 A1* | 9/2018 | Aki | G01N 37/00 |
| 2022/0074533 A1* | 3/2022 | Banchieri | F16K 11/072 |

FOREIGN PATENT DOCUMENTS

| | | |
|---|---|---|
| KR | 10-1515020 B1 | 4/2015 |
| KR | 10-1770796 B1 | 8/2017 |
| KR | 10-2018-0110094 A | 10/2018 |

\* cited by examiner

|  | Proposed Microfluidic Platform ELISA | | Conventional ELISA[6] | | Conventional ELISA as suggested in Enzo manual | |
|---|---|---|---|---|---|---|
| Antigen/enzyme-linked 2nd Ab/enzyme substrate/detection method | cTnI/AV-HRP 2nd Ab/HRP substrate/ colorimetric analysis using android app | | cTnI/ Monoclonal (M) Ab /HRP substrate/ colorimetric analysis using ELISA reader | | cTnI HV-HRP 2nd Ab/TMB substrate / colorimetric analysis using ELISA reader | |
| Time and reagents | Volume [µL] | Time [min] | Volume [µL] | Time [min] | Volume [µL] | Time [min] |
| Antigen immobilization | 15 | 10 | 100 | 60 | 100 | 60 |
| Antibody complexing | 15 | 10 | 100 | 8 * 60 | 100 | 60 |
| Signal amplification | 15 | 15 | 100 | 30 | 100 | 20~30 |

FIG. 13

MICROFLUIDIC CONNECTION DEVICE

CROSS REFERENCE TO RELATED APPLICATIONS

This application claims priority to Korean Patent Application No. 10-2018-0153517, filed on Dec. 3, 2018. Further, the application is the National Phase application of International Application No. PCT/KR2019/012926, filed on Oct. 2, 2019, which designates the United States. Each of these applications is hereby incorporated by reference in their entirety into the present application.

TECHNICAL FIELD

The present invention relates to a connection device that enables observation of a fluid chemical reaction with a very small amount of fluid, and in particular, to a microfluidic connection device that enables a rapider reaction observation of a fluid chemical reaction with a much smaller amount of samples than a conventional reaction experiment using a 96-well used for sample reaction.

BACKGROUND ART

Enzyme-linked immunosorbent assay (hereinafter referred to as "ELISA") is a method of measuring the amount of antigen or antibody using an antigen-antibody reaction with an enzyme as a marker.

ELISA is widely used as an analysis tool for quantitative investigation of antigens/antibodies inside an analyte in the fields of clinical medicine, environment, food contamination monitoring, etc. ELISA is consist of simple processes, and is an efficient multi-analysis tool with high sensitivity and selectivity.

The process of the conventional ELISA is performed using a 96-well plate that has ninety six densely, horizontally and vertically formed insertion holes into which each of ninety six sample beakers or tubes are inserted respectively, so that the data that can be read in colors is provided after a relatively long period of time. In addition, since the required amount of sample should be sufficient to fill a beaker or a tube to a certain level, it costs a significant price to perform the process, especially in the case of an expensive sample. Therefore, it is extremely difficult to apply the conventional method due to a problem that it takes a long time, and a cost problem especially when immediate diagnosis is required in the field.

In the conventional ELISA, a 96-well plate is utilized, and it is based on a basic immunological concept in which a single antigen is bound to a specific antibody for that single antigen. So, in order to perform an immunoassay that requires to take several steps, each reaction step requires to wash away the substances other than the necessary substances out of reactants, and needs a process of transporting and injecting reagents with a pipette, and it takes a long time to react such sufficient amount of sample that may be observed with the naked eyes.

However, antibody immunoreactions are widely used not only for academic experiments in research institutes, but also for urgent prescriptions in a wide range of hospital sites, so they need to be carried out quickly for urgent treatment. But, since the conventional ELISA process takes considerable time, cost, and effort, it cannot meet the needs of on-site medical care so that many patients cannot receive treatment through accurate diagnosis in a timely manner.

Reaction process with ELISA includes a process in which a measurement sample such as blood or plasma is supplied to a substrate on which the capture antibody is immobilized and the target antigen present in the sample is bound to the capture antibody as shown in FIG. 1, a process of binding the labeled antibody to the capture antibody-antigen conjugate in the form of a sandwich, and a process of finally bonding the enzyme substrate to the labeled antibody. At this time, in each reaction step, it is required to inject a sample such as an antigen or an antibody and wait for reaction for a long time, and it also requires a process of washing and removing unnecessary reactants in the middle of each reaction. Therefore, it consumes an enormous amount of time for one immunoreaction, and when a conventional 96-well plate is used, a considerable amount of expensive sample is used so that the reaction can be visually determined, resulting in considerable cost.

Therefore, there is a request for a technology for a reaction device that enables antibody immunoreaction analysis much faster than the 96-well plate used in the conventional ELISA, and requires much cheaper cost as the analysis can be performed with a very small amount of sample, and performs a plurality of reaction processes that include intermediate washing so that the intermediate washing is carried out automatically, thereby reducing the labor of the experimenter.

DOCUMENTS OF RELATED ART

Korean Patent No. 10-1515020 (publication date: Apr. 24, 2015)

DISCLOSURE

Technical Problem

Accordingly, the present invention provides a microfluidic connection device that enables antibody immunoreaction analysis much faster than the 96-well plate used in the conventional ELISA, and requires much cheaper cost as the analysis can be performed with a very small amount of sample, and performs a plurality of reaction processes that include intermediate washing so that the intermediate washing is carried out automatically, thereby reducing the labor of the experimenter.

Technical Solution

In an embodiment of the present invention, a microfluidic connection device according to an embodiment of the present invention comprises: a microvalve consisting of microtubes in form of a micro tube, and a fluid transfer unit that flows or stops samples filled in the microtubes; a base plate; reaction zones installed on the upper surfaces of the plates, and having observation windows through which chemical reactions between samples supplied to therein through the microtubes are observed; supply tubes connecting the microtubes to the reaction zones; and a reaction plate consisting of discharge tubes for discharging reactants from the reaction zones.

Preferably, the reaction zones are formed at the upper ends of the reagent lifting columns installed on the upper surface of the plate in form of columns, and the areas where the supply tubes and the discharge tubes are connected to the reaction zones are elongated in a vertical direction in the reagent lifting columns.

Preferably, the reaction zones are formed on the upper surfaces of the reagent lifting columns with a predetermined area, the reaction zones are protected by a sealing covers that seal the upper parts of the reagent lifting columns, and the observation windows are formed in the centers of the sealing covers.

Preferably, the reagent lifting columns, the reaction zones, and the sealing covers are formed in parallel on the upper surface of the plate, and a plurality of microtubes are installed to correspond to the number of the reagent lifting columns.

In this case, desirably, the microvalve comprises: a plate-shaped body; a plurality of microtubes embedded in parallel to each other in the body; a plurality of bumpers installed in longitudinal direction over some sections of the area where the microtubes are embedded; a pressure roller bar being a member in form of a rod having a circular cross section, installed on the upper parts of the bumpers so that its longitudinal direction crosses the bumpers, and for pressurizing a plurality of the bumpers at the same time by moving while rolling along the upper parts of the bumpers; and a drive unit for moving the pressure roller bar or the body along the direction of the microtubes, wherein the body has a plurality of microchannels formed in parallel to each other therein, wherein the microtubes are embedded in the microchannels, wherein the body and the bumpers are made out of elastic material, so that when either the pressure roller bar or the body is moved due to the drive unit, the pressure roller bar rolls along the upper portions of the bumpers to press the bumpers, thereby transferring samples filled in the microtubes by movement of compression areas formed by pressing the bumpers, the microchannel and the microtube with the pressure roller bar.

The microfluidic connection device according to the present invention further comprises: a suction pump installed at the discharge tube, for taking in a plurality of samples filled in the microtubes under the pressure release sections so as to transfer a plurality of the samples toward the reaction zones when the pressure roller bar reaches the upper part of the pressure release sections, wherein the pressure release sections in which the bumpers are disconnected, are famed on the upper part of the microchannels, wherein the pressure release sections are formed to deviate from each other for each of a plurality of the microchannels, wherein when the pressure roller bar that is rolling on the upper part of the bumpers reaches the upper parts of the pressure release sections, the microtubes and the microchannels are released from compression.

Furthermore, the pressure release sections are formed to meet the pressure roller bar sequentially from the microchannel at one end to the microchannel at the other end among a plurality of the microchannels while the pressure roller bar is rolling to advance.

Preferably, all discharge tubes each of which is provided for each of the reaction zones are connected to the one discharge hole, and the suction pump is installed to be connected to one discharge hole.

On the other hand, preferably, the microvalve further consists of: a base installed under the body; a rotation support bracket fixedly installed on both sides of the base, having bearings therein, and coupled to both ends of the pressure roller bar so as to rotatably fix the pressure roller bar; and a linear motor for advancing or reversing the microvalve between the bearing and the pressure roller bar.

Advantageous Effects

Furthermore, a microfluidic connection device according to the present invention enables antibody immunoreaction analysis much faster than the 96-well plate used in the conventional ELISA, and requires much cheaper cost as the analysis can be performed with a very small amount of sample, and performs a plurality of reaction processes that include intermediate washing so that the intermediate washing is carried out automatically, thereby reducing the labor of the experimenter.

DESCRIPTION OF DRAWINGS

FIG. 13 is a comparison table of the ELISA process according to the present invention and the conventional ELISA processes.

BEST MODE

Figure 1:
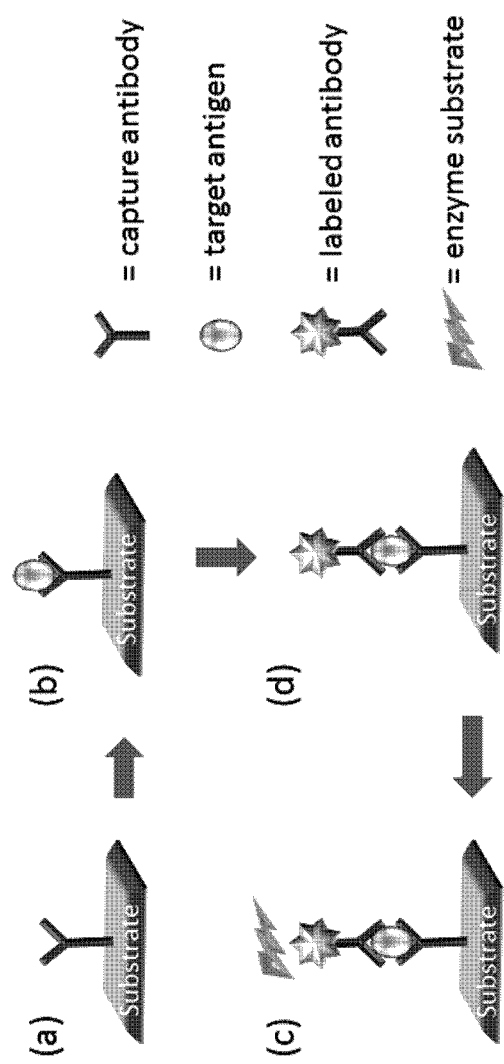
FIG. 1 shows a conceptual view of an immunoreaction performed by the reaction device according to the present invention.

Specific structural or functional descriptions presented in the embodiments of the present invention are exemplified for the purpose of describing the embodiments according to the concept of the present invention only. The embodiments according to the concept of the present invention may be implemented in various forms. In addition, it should not be construed as limited to the embodiments described in the present specification, and should be understood to include all modifications, equivalents, and substitutes that belong to the spirit and scope of the present invention.

Hereinafter, the present invention will be described in detail with reference to the accompanying drawings.

The microfluidic connection device according to the present invention is composed of a reaction plate 10 as shown in FIG. 2.

The reaction plate 10 is composed of a plate-shaped plate 11, reaction zones 15 where a chemical reaction occurs between samples supplied through the microtubes 24, which have observation windows for observing the chemical reaction and are installed on the upper surface of the plate, supply tubes 13 connecting the reaction zones 15 with the microtubes 24, and discharge tubes 14 for discharging the reactants from the reaction zones 15.

Here, column-shaped reagent lifting columns 12 are installed on the upper surface of the plate 11, and the reaction zones 15 are formed at the upper ends of the reagent lifting columns 12. The supply tubes 13 and the discharge tubes 14 are both elongated in a vertical direction in the reagent lifting columns 12 to be connected to the reaction zones 15 formed at the upper ends of the reagent lifting columns 12.

Figure 2A:
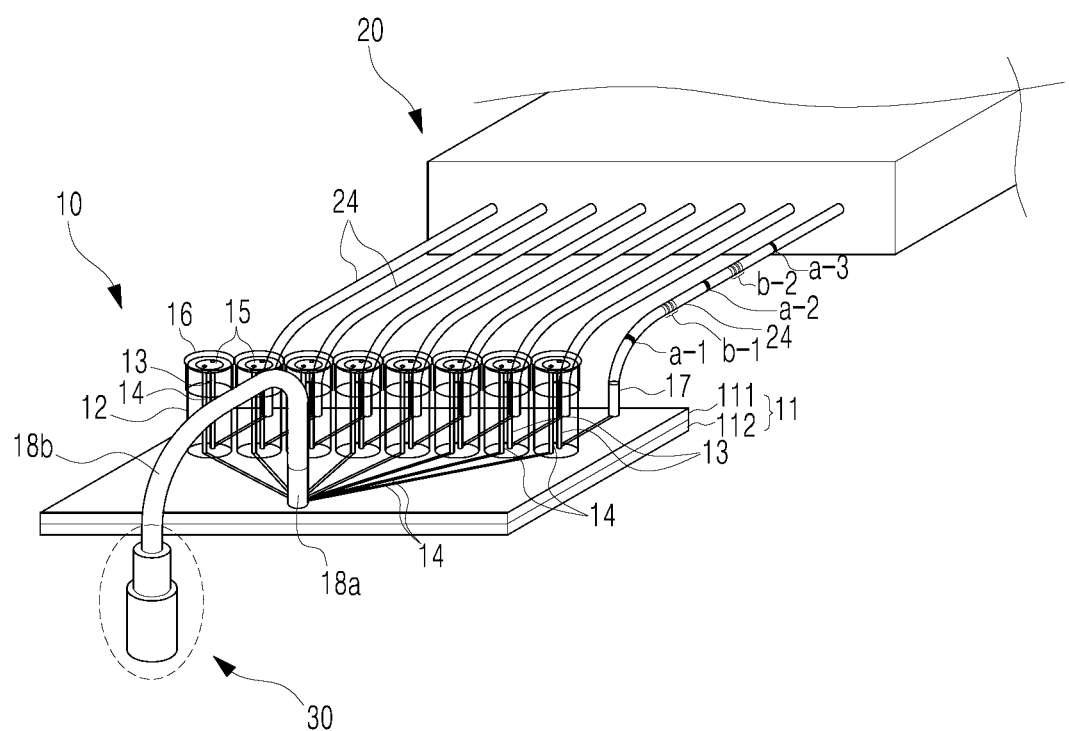
FIG. 2A shows a schematic perspective view of a reaction device according to the present invention.

Since the reagent lifting columns 12 are manufactured in column shapes as shown in FIG. 2A, they have the same shape as beakers or microbeakers that are densely inserted into a 96-well plate used in a conventional antibody immunoreaction experiment. Therefore, it can be used together with equipment required for analysis experiments using various 96-well plates such as ovens or cyclers manufactured to process conventional 96-well plates.

However, since the reaction zones 15 are installed on the upper surfaces of the reagent lifting columns 12, the reactions proceeds only in spaces of thin volumes formed on the upper surfaces of the reagent lifting columns 12. So, it enables the analysis experiment which has been carried out in a conventional 96-well plate, even if there is only a very small amount of reagent or the object to be measured since the required amount of the object to be measured is remarkably less than conventional 96-well plate.

In addition, the reaction zones 15 are formed on the upper surfaces of the reagent lifting columns 12, and the supply tubes 13 for supplying reagents or objects to be measured to the reaction zones 15 and the discharge tubes 14 for discharging the reactants from the reaction zones 15 are installed in the vertical direction in the inner spaces under the reagent lifting columns 12. So, although the amount of the required sample is extremely small, the area where the reaction occurs are located in the reaction zones 15 which are the top portions most easily observed, so that the reaction is more easily observed compared to the conventional 96-well plate.

Figure 2B:
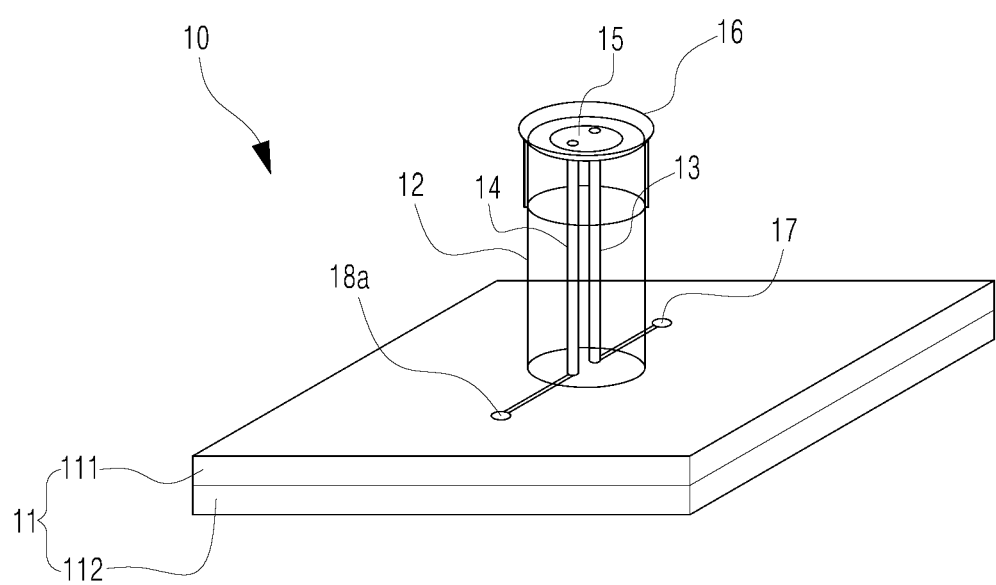
FIG. 2B shows an enlarged perspective view of the reagent lifting column shown in FIG. 2A.

As shown in FIGS. 2A and 2B, an observation window is formed on the top of the reaction zone 15 which is formed on the upper surface of the reagent lifting column 12 for easy observation. However, in FIGS. 2A and 2B, the observation window is so transparent that it may not be visible, but there is an observation window at the top of the reaction zone 15. In particular, the observation window is formed in the center of the upper surface of the sealing cover 16 that seals the upper portion of the reagent lifting column 12.

The sealing cover 16 seals the upper part of the reagent lifting column 12 as well as the reaction zone 15 as shown in FIG. 2B. The sealing cover 16 is particularly detachably coupled to the reagent lifting column 12. So, If it is urgently needed to collect the reactants, the sealing cover 16 is separated from the reagent lifting column 12 so that the reactants can be collected directly from the reaction zone 15. In addition, even when disinfection and precise cleaning of the reaction zone 15 are required, disinfection and cleaning are possible by removing the sealing cover 16 from the reagent lifting column 12. At this time, it is also possible to clean the conventional 96-well plate with specialized equipment commonly used.

The reaction zone 15 is formed at an area where the inner ceiling of the sealing cover 16 and the upper surface of the reagent lifting column 12 meet. The space formed by the reaction zone 15 is specifically a space formed by processing the upper surface of the reagent lifting column 12 to have a pattern having a certain shape such as the long hexagonal shape shown in FIG. 3A. Therefore, when the sealing cover 16 is coupled to the upper surface of the reagent lifting column 12, the processed pattern-shaped space becomes the reaction zone 15.

At this time, the capture antibody is immobilized on the inner ceiling of the sealing cover 16, that is, the lower surface of the observation window. Immobilization of the capture antibody is the same as the commercially available product in which a certain capture antibody is immobilized inside the well in the case of a 96-well used in a typical immunoreaction experiment.

The conventional 96-well consists of twelve rows of wells. Each row of wells consists of eight wells and are manufactured to be connected side by side with each other. At this time, a row of eight wells can be used as eight sealing covers 16 connected to each other as shown in FIG. 2A.

In particular, since the commercially available sealing covers 16 consisting of eight wells shown in FIG. 2A have capture antibodies that have already been immobilized to the inner ceilings, a commercially available 96-well can be immediately used as the sealing covers 16 of the present invention without separately manufacturing sealing covers or separately immobilizing the capture antibodies to the manufactured sealing covers in the present invention.

When the commercially available sealing covers 16 consisting of eight wells are coupled to the upper portions of the eight reagent lifting columns 12, the upper surfaces of the reagent lifting columns 12 are sealed due to the eight wells, and the reaction zones 15 are sealed. So, an antigen-antibody reaction can be performed with the capture antibodies.

Figure 3A:
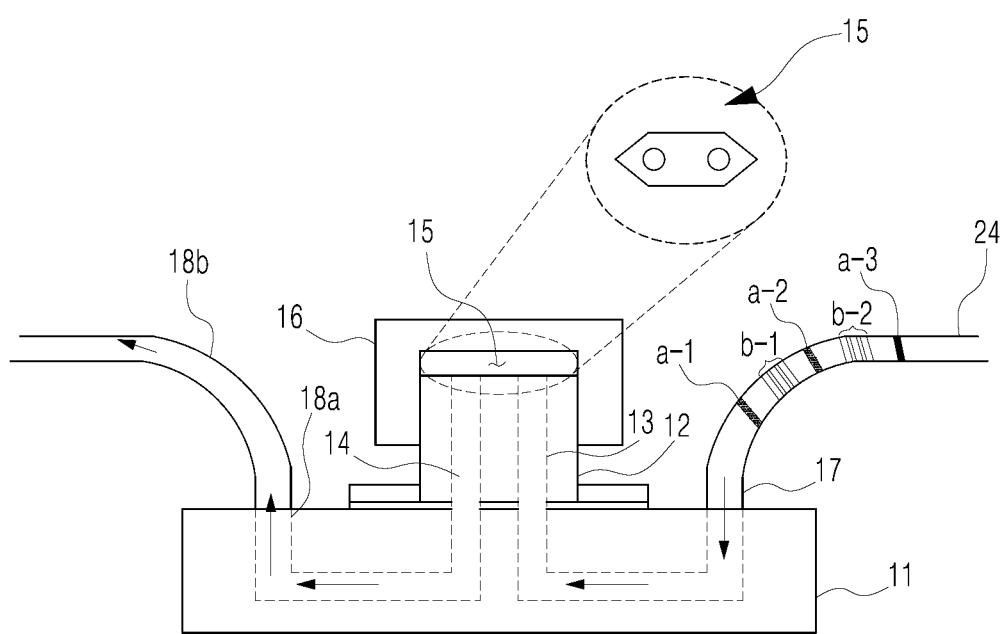
FIG. 3A shows a side cross-sectional view of FIG. 2B.
Figure 3B:
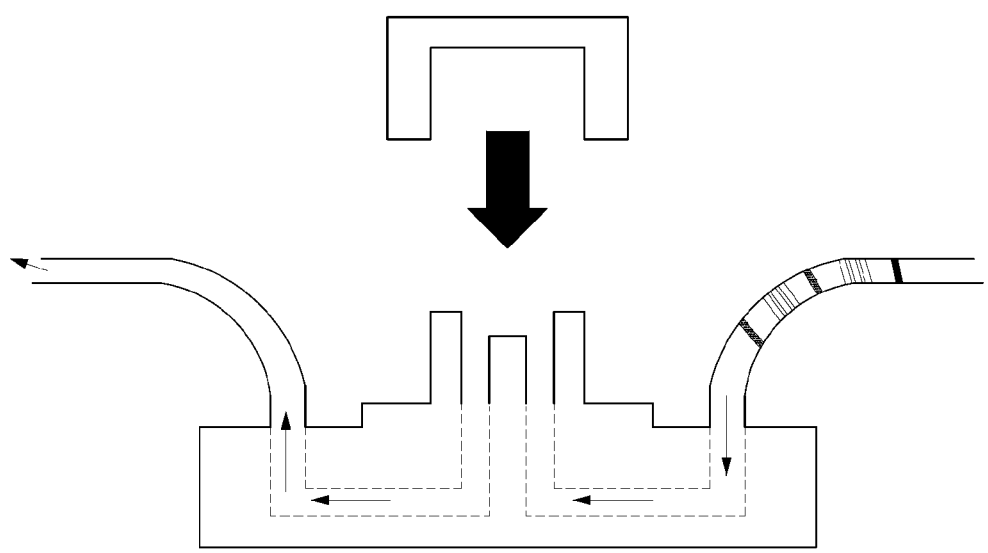
FIG. 3B shows an exploded view of FIG. 3A.

As shown in FIGS. 2B and 3A, the reaction zone 15 receives a sample or an object to be measured from the supply tube 13, and discharges the substance remaining after the reaction or the substance washed away after intermediate washing through the discharge tube 14. The reaction zone 15 has a planar shape in the form of a hexahedron as shown in FIG. 3A, but there is no particular limitation on the shape of the reaction zone 15 and may be formed in a circular shape as in FIG. 2B. The reaction zone 15 has a certain area, but the distance between the observation window and the reaction zone 15, that is, the height of the space that makes up the reaction zone 15 is very small, so the reaction can be performed with only a very small amount of sample or object to be measured. Therefore, the microfluidic reaction device according to the present invention requires such extremely small amount of sample for the reaction that only a small amount is required even for an expensive sample. So, compared to the prior art, the required cost is significantly reduced in the present invention.

The supply tube 13 and the discharge tube 14 are connected to the injection hole 17 and the discharge hole 18a, respectively, as shown in FIGS. 2B and 3A. The injection hole 17 and the discharge hole 18a may be in the form of a simple hole as shown in FIG. 2B, and it may also include a short tube protruding above the plate 11 as shown in FIGS. 2A and 3A.

The supply tube 13 and the discharge tube 14 are embedded horizontally in plate 11 in the section from the lower end of the reagent lifting column 12 to the injection hole 17 or the discharge hole 18a, as shown in FIGS. 2B and 3A.

Figure 3C:
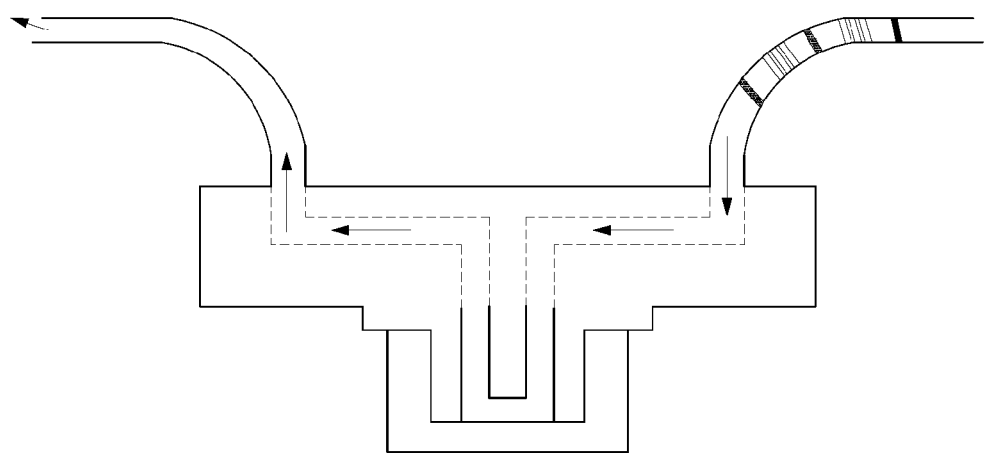
FIG. 3C shows a side cross-sectional view of a modified embodiment shown in FIG. 3A.
Figure 4:
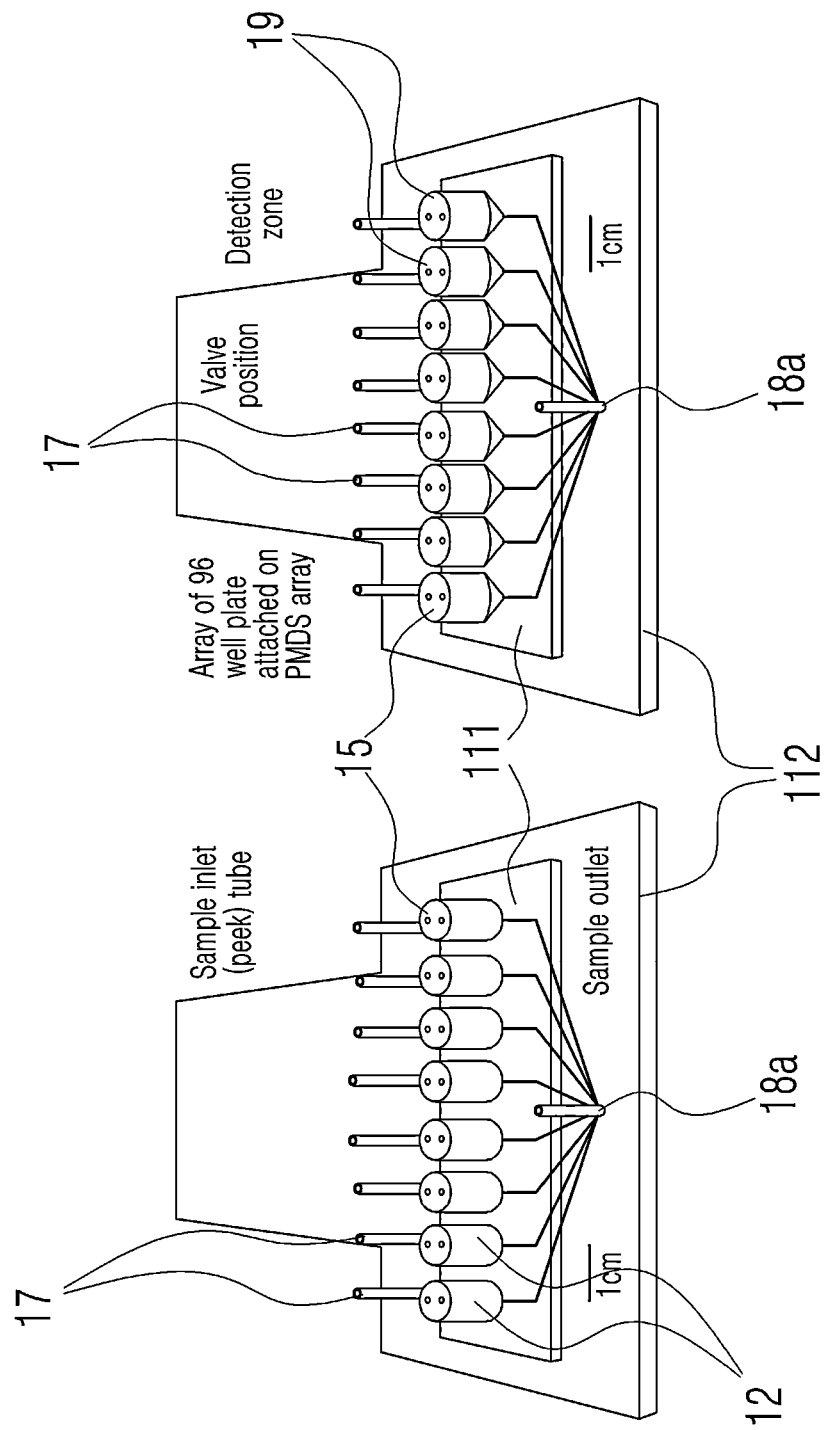
FIG. 4 is a photograph showing the reaction plate shown in FIG. 2A.

Furthermore, the reagent lifting column 12 may be formed on the bottom surface of the plate 11 as shown in FIG. 3C. At this time, the injection hole 17 and the discharge hole 18a are formed on the upper surface of the plate 11. This configuration is made because a conventional 96-well can be used as a sealing cover, and when a fluid material is embedded in the 96-well, the reaction can be observed due to the combination and configuration as shown in FIG. 3C.

Any material that is inexpensive and has good chemical resistance can be selected for the plate 11. Materials having good transparency, very strong durability, and good workability, such as PDMS (polydimethylsiloxane) may be selected as the material of the plate 11.

The plate 11 may be manufactured by overlapping two plates 111 and 112. At this time, the horizontal portions of the supply tube 13 and the discharge tube 14 can be made by inserting tubes between the two plates constituting the plate 11, that is, the upper plate 111 and the lower plate 112, or by forming horizontal grooves on the bottom surface of the upper plate 111 or on the upper surface of the lower plate 112. The bottom surface of the upper plate 111 and the upper surface of the lower plate 112 are the contact portions that the upper plate 111 and the lower plate 112 contact each other.

In addition, a microvalve 20 for supplying a sample to the reaction plate 10 may be connected to the reaction plate 10.

The microvalve 20 includes microtubes 24 in the form of microtubes, and a fluid transfer unit for moving the sample when the microtubes 24 are filled with samples. The microvalve 20 will be described in detail later with reference to FIGS. 5 through 8.

In the present invention, as in the embodiment shown in FIG. 2A, a plurality of reagent lifting columns 12 are arranged side by side on the upper surface of the plate 11. Accordingly, as in a conventional 96-well plate, a plurality of related reaction experiments can be performed simultaneously. At this time, each of a plurality of microtubes 24 for connecting the microvalve 20 and the reaction plate 10 are also connected to each of the reagent lift columns 12 as many as the number of reagent lift columns 12 as shown in FIG. 2A.

Figure 5:
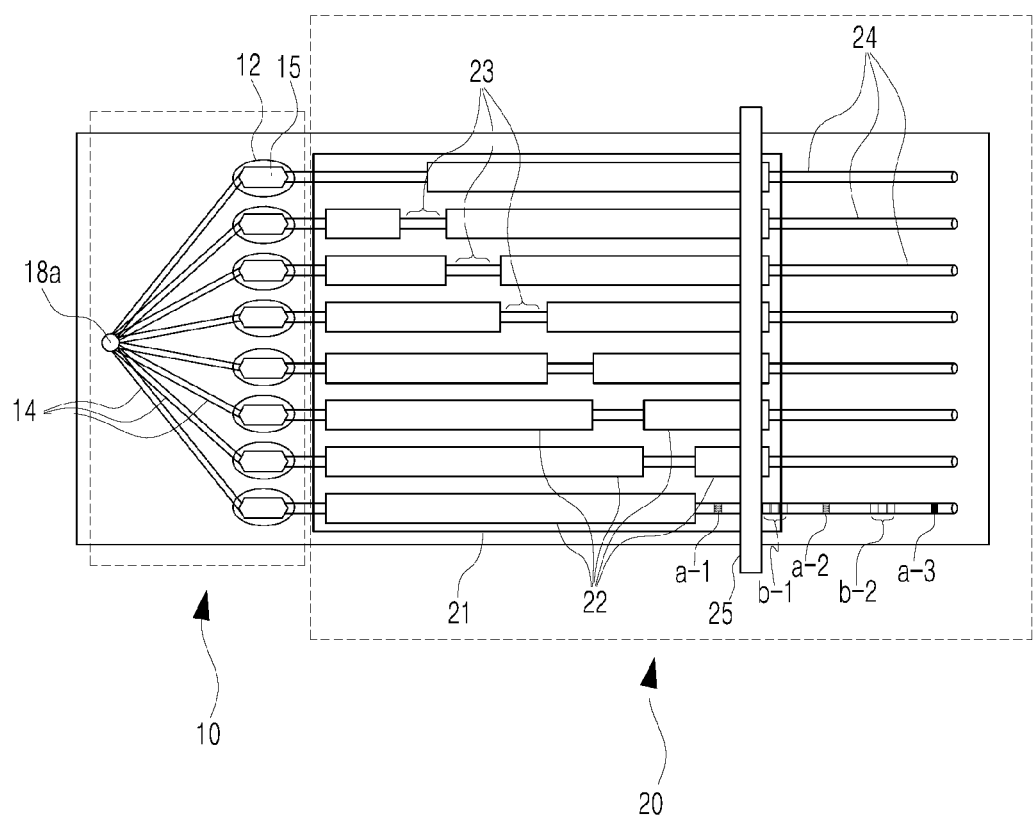
FIG. 5 shows a partial plan view of the microvalve shown in FIG. 2A.

As shown in FIG. 5, the microvalve 20 comprises: a plate-shaped body 21; a plurality of microtubes 24 embedded in parallel to each other in the body 21; a plurality of bumpers 22 installed in longitudinal direction over some sections of the area where the microtubes 24 are embedded; a pressure roller bar 25 which is a member in the form of a rod having a circular cross section, installed on the upper parts of the bumpers 22 so that its longitudinal direction crosses the bumpers 22, and pressurizes a plurality of the bumpers 22 at the same time by moving while rolling along the upper parts of the bumpers 22; and a drive unit (not shown) for moving the pressure roller bar 25 or the body 21 along the direction of the microtubes 24.

Figure 6A:
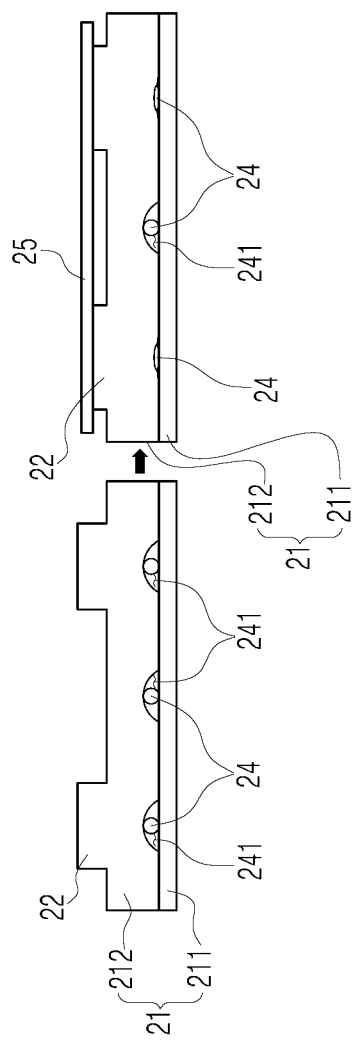
FIG. 6A shows a front cross-sectional view depicting the principle of the upper bumper of the channel shown in FIG. 5.

According to the embodiment shown in FIG. 6A, the body 21 in which the microtubes 24 are embedded may be formed by overlapping the upper plate 212 and the lower plate 211. Here, the microchannels 241 are famed on the bottom surface of the upper plate 212, and the upper plate 212 is formed of an elastic material. So, when a pressure is applied to the bumpers 22 above microchannels 241, the pressure is transmitted through the upper plate 212, so the microchannels 241 are deformed flat as shown on the right side of FIG. 6A. When the microchannels 241 are flattened under pressure, the microtubes 24 embedded in the microchannels 241 are also deformed flat and clogged as shown in FIG. 6A. Hereinafter, the area at which the microtubes 24 become flat will be referred to as 'compression areas'.

Since the 'compression areas' are formed in the vertical lower part of the pressure roller bar 25, when the pressure roller bar 25 moves along the upper parts of the bumpers, the compression areas also move together with the pressure roller bar 25. However, the pressure roller bar 25 may either move or only rotate in place and the body 21 in which the microtubes 24 are embedded may move instead. The direction of movement is the longitudinal direction of the bumpers 22 formed along the longitudinal direction of the microtubes 24.

As shown in FIGS. 5 and 6A, the bumpers 22 transmit the pressure of the pressure roller bar 25 to the microtubes 24 so as to seal certain areas of the microtubes 24. The microtubes 24 are sealed at the very compression areas, and the compression areas prevent the reagents or the objects to be measured filled in the microtubes 24 from moving when the pressure roller bar 25 and the body 21 are both stopped.

However, if only when one of the pressure roller bar 25 or the body 21 moves, a samples or objects to be measured (hereinafter, referred to as 'sample or the like') filled in the microtubes 24 are moved, then the control of the moving distance of a fine sample or the like depends only on the pressure roller bar 25, so that a plurality of microtubes 24 are arranged in parallel as shown in FIG. 5 and the sample or the like is filled at different location corresponding to a desired reaction time in each microtube 24. So, the samples or the like moving inside the microtubes 24 arrive at a different time. Due to the error during movement, however, the moving speed or the order of the sample or the like inside each microtube 24 may vary.

Therefore, in the present invention, a pressure release sections 23 and a suction pump 30 are provided in order that the samples or the like filled in the microtubes 24 may reach the reaction zones 15 sequentially in order according to the experiment plan.

The pressure release sections 23 are sections where the bumpers 22 are disconnected as shown in FIG. 5. The sections where the bumpers 22 are disconnected are not crushed because the microchannels 241 and the microtubes 24 are not subjected to pressure even when the pressure roller bar 25 presses the sections from the top as shown on the right side of FIG. 6A. Therefore, when air is blown or sucked from either side of the microtubes 24, the samples or the like get ready to be moved accordingly.

The suction pump 30 is connected to the discharge hole 18a formed in the reaction plate 10 as shown in FIG. 2A. One discharge hole 18a is formed in the reaction plate 10, and a plurality of the discharge tubes 18b which are connected to each of a plurality of the reaction zones 15 and discharge the reaction residue from the reaction zones 15 are all connected to one discharge hole 18a. It is not only because if the suction pump 30 is installed for each of a plurality of the discharge tubes 18b, the cost will also increase but also because if it is necessary to control a plurality of suction pumps 30 to control the speed of the sample or the like that reaches each reaction zone 15, a control system for sequentially controlling the suction pumps 30 is also required, thereby increasing the cost required for this too.

Accordingly, in the present invention, one suction pump 30 is provided for one discharge hole 18a and the pressure release sections 23 are sequentially formed in the bumpers 22 in a desired reaction order. And, when the relative motion between the pressure roller bar 25 and the body 21 occurs and the pressure release sections 23 formed on the upper portions of microtubes 24 and the pressure roller bar 25 meet, the pressure is released at the microtubes 24. Here, when the suction pump 30 is operated, the samples or the like are moved only within the microtubes 24 where the pressure is released.

The pressure release sections 23 are also formed sequentially in a desired reaction order. As shown in FIG. 5, since the suction pump 30 is installed, the reactions proceed at the reaction zones 15 connected to the pressure release sections 23 in the order of meeting the pressure release sections 23 during the pressure roller bar 25 moves.

Referring to FIG. 6A, all of the microtubes 24 other than the microtubes 24 where the pressure release sections 23 are formed are compressed by the pressure roller bar 25. Since only the microtubes 24 where the pressure release sections 23 are located under the pressure roller bar 25 are opened, the samples or the like are moved only in the opened microtubes 24 and they enter the reaction zones 15 when the suction pump 30 is operated.

In addition, since the suction pump 30 is installed, even if the pressure roller bar 25 does not move several times to push the samples or the like, the samples or the like were made to reach the reaction zones 15 at once by the suction force as soon as the pressure roller bar 25 is positioned above the pressure release sections 23. Therefore, the entire reaction analysis process can be quickly performed due to the interaction between the suction pump 30 and the pressure release sections 23.

On the other hand, when the samples or the like move toward the reaction zones 15 by the operation of the suction pump 30, the residues other than the substances required after any one reaction need to be discharged in order for a series of two or more reactions to occur in one reaction zone 15d. Therefore, as shown in FIG. 3A, the first washing solution b-1 and the second washing solution b-2 are filled between the first reagent a-1 and the second reagent a-2, and between the second reagent a-2 and the third reagent a-3 respectively, so as to wash the reaction zone 15. So, the next reaction can be prepared. As an example in which such a series of reactions occurs in one place, there may be mentioned the ELISA described with reference to FIG. 1 in the section BACKGROUND OF THE INVENTION. In this case, the first antibodies are coated on the reaction zones 15 in advance, the first reagent a-1 is the target antigen, the second reagent a-2 is a second antibody bound in a sandwich form, and the third reagent a-3 becomes an enzyme substrate.

Since such a series of reactions occur at the bottom of the beaker in a conventional 96-well plate, observation was rather difficult even though a significant amount of expensive sample was required, but in the present invention, reactions can be observed at the optimal observation position even with a very small amount of sample.

Figure 6B:
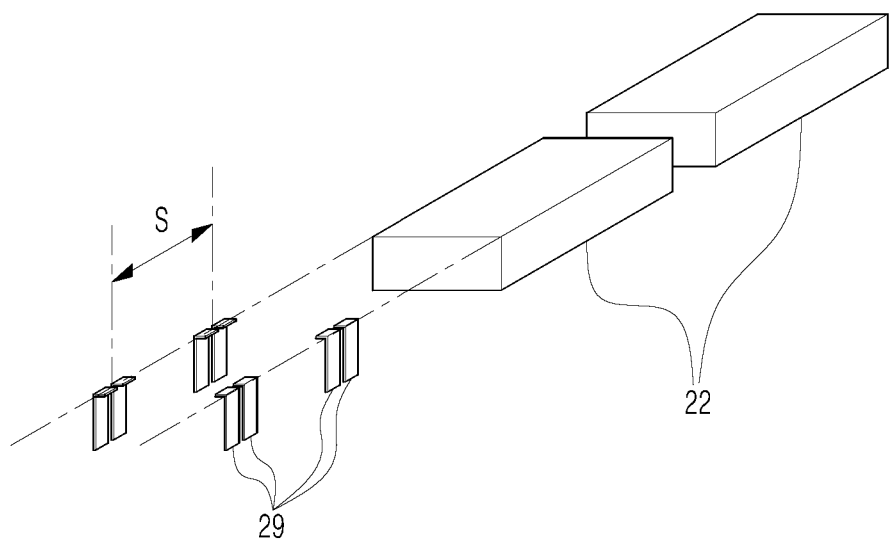
FIG. 6B shows a perspective view of a modified embodiment of a channel upper bumper.

In addition, there may be a case where the position of the pressure release sections 23 need to change or adjust between the microchannels 24 according to the needs for the experiment. In preparation for this case, the bumpers 22 are separately manufactured to be separated from the upper plate 212 so that the pressure release sections 23 can be formed in the desired sections as shown in FIG. 6B. And, the bumpers 22 are manufactured in the form of a module with a certain length and a bumper gripping protrusion 29 to which the bumpers 22 are detachably fixed may be formed on the upper surface of the upper plate 212.

The bumper gripping protrusion 29 may be installed so that its one end and other end are fixed in the longitudinal direction of the bumpers 22 as shown in FIG. 6B. Here, the bumper gripping protrusion 29 is also made out of an elastic material. Therefore, when the pressure roller bar 25 passes, the bumper gripping protrusion 29 does not hinder the bumpers 22 from contracting, and the bumpers 22 and the bumper gripping protrusion 29 may be compressed together.

In the process of pressing the bumpers 22 while the pressure roller bar 25 moves along the upper parts of the bumpers 22, the pressure roller bar 25 itself may be moved along the longitudinal direction of the bumpers 22, or the body 21 constituting the microvalve 20 may be itself moved while the pressure roller bar 25 is fixed in place and rotated only.

Figure 7:
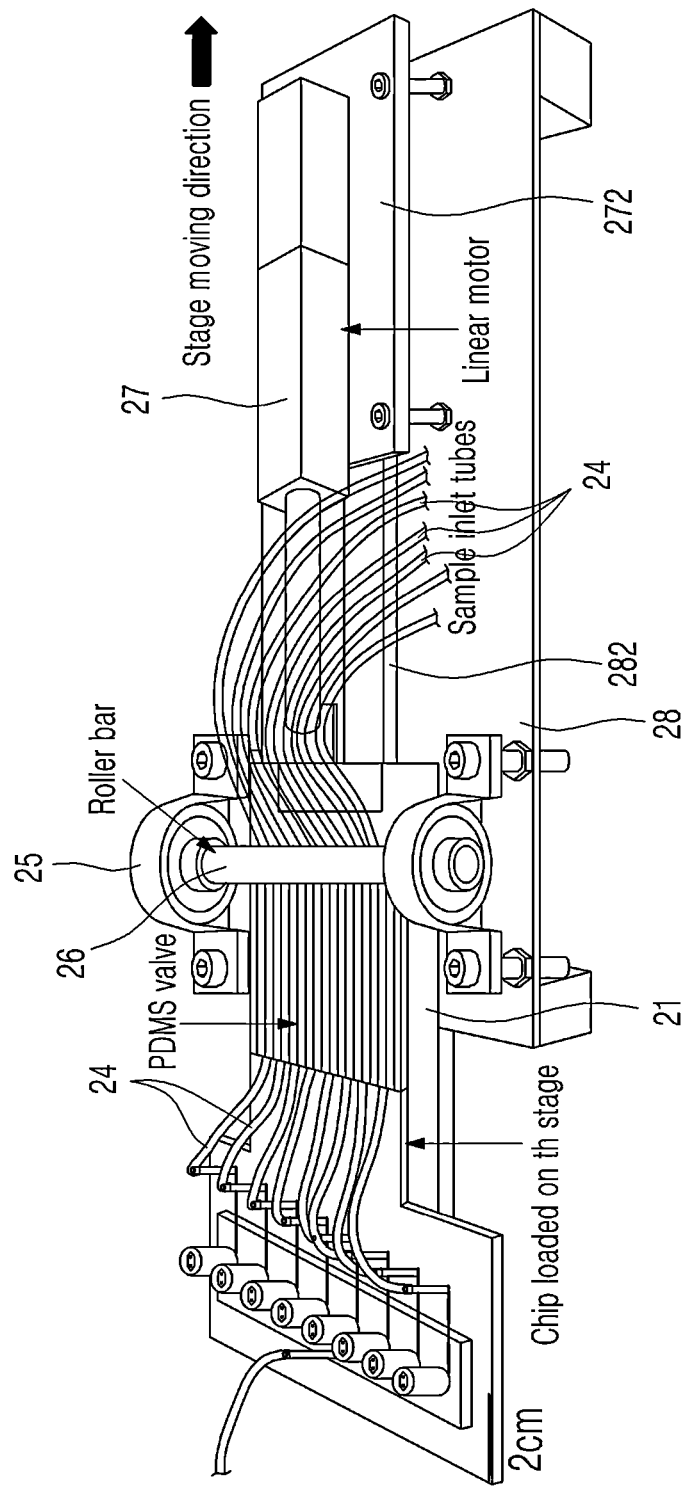
FIG. 7 is a photograph showing the overall configuration of the micropump in FIG. 2A.

In the embodiment shown in FIG. 7, the bumpers 22 is rotated in place and the body 21 moves. For this operation, the microvalve 20 further comprises: a base 28 installed under the body 21; a rotation support bracket 26 fixedly installed on both sides of the base 28 and having bearings (not shown) therein and coupled to both ends of the pressure roller bar 25 to rotatably fix the pressure roller bar 25; a linear motor 27 for advancing or reversing the body 21 between the bearing and the pressure roller bar 25. In this case, when the reaction plate 10 and the body 21 constituting the microvalve 20 are fixedly coupled together and move, the microtubes 24 are prevented from being pulled out of the injection holes 17 and separated from the injection holes 17 due to the applied tension even if the microtubes 24 are not made manufactured longer than necessary.

Owing to the configuration in this way, the process of pulling the body 21 only once by the linear motor 27 completes all series of reactions for each reaction zones 15, and all the reactions in the reaction zones 15 can be sequentially completed in the desired order. At this time, the linear motor 27 stops when the pressure roller bar 25 is positioned at any one pressure release section 23. From then on, the suction pump 30 collects the samples a-1, a-2 and a-3 and the washing liquids b-1 and b-2 sequentially through the microtubes 24 with the pressure release sections 23 open. All sequential reactions are performed in the reaction zones 15 connected to the microtubes 24 where the pressure roller bar 25 is located at the upper portions of the pressure release sections 23, and the linear motor 27 is stopped during this time.

Figure 8:
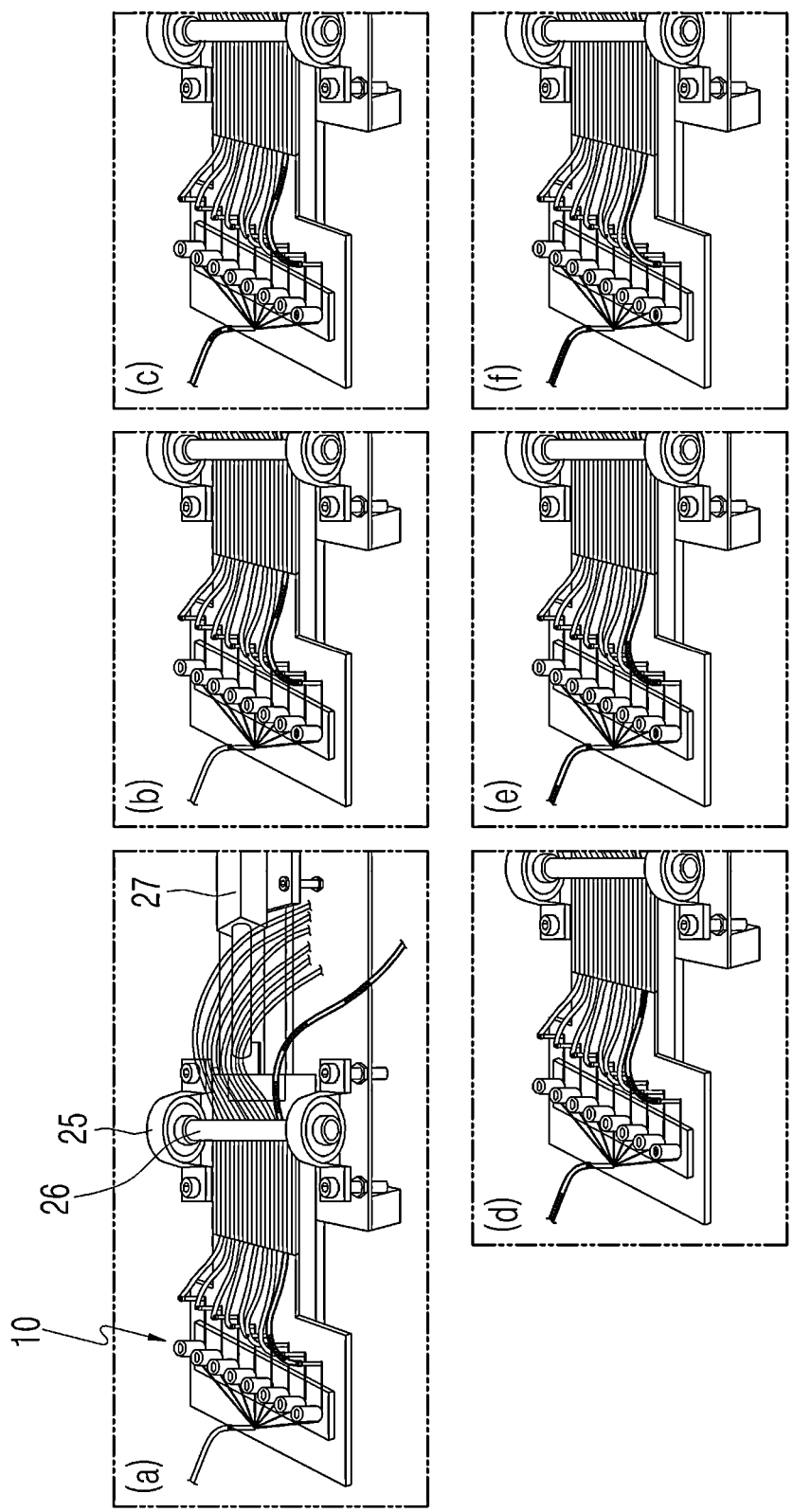
FIG. 8 is a photograph showing the operating sequence of the micropump of FIG. 7.

This process is shown in the photograph of FIG. 8. In FIG. 8, the reaction proceeds in the order of (a), (b), (c), (d), (e) and (f).

Figure 9:
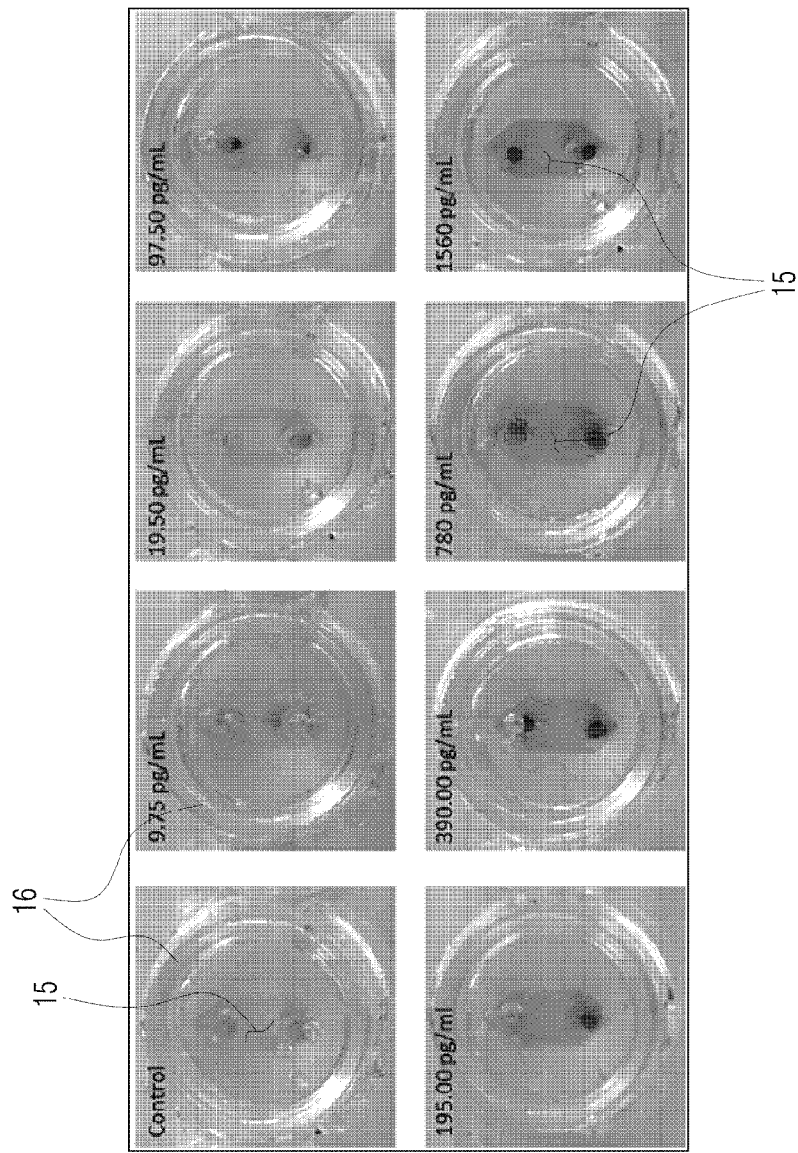
FIG. 9 is a photograph showing the color differences among seven concentrations of cTnI.

On the other hand, the amount of sample required for the reaction to proceed clearly is shown in the photograph of FIG. 9. The eight pictures shown in FIG. 9 are taken from the above of the reaction zones 15, and each picture shows the degree of reaction of a different amount of sample administered by the intensity of the color.

The photographs of FIG. 9 is a color change of the reaction zones when the reaction of the same procedure as the actual ELISA procedure for quantitatively detecting cardiac troponin I (cTnI) protein is performed in the microfluidic reaction device according to the present invention. Here, the first antibodies are coated in the reaction zones 15. And, 15 μL cTnI antigen (cTnI protein, Enzo Biosemic, USA), 45 μL washing solution, and secondary antibody conjugated with 15 μL HRP substrate were sequentially passed through here first, and the antigen binding reaction, washing, and secondary antibody binding reaction proceed in order.

In this case, the color change corresponding to the eight different types of the concentrations of cTnI in the 15 μL cTnI antigen is shown in FIG. 9. At this time, a clear detection reaction was observed at the concentration of 97.5 pg/mL. At concentrations above 390 pg/mL, the color is the same even if the concentration of cTnI is increased. So, even if a clear reaction observation is desired, it can be seen that a successful experimental process can be performed only with cTnI at a concentration of 390 pg/mL.

Figure 10:
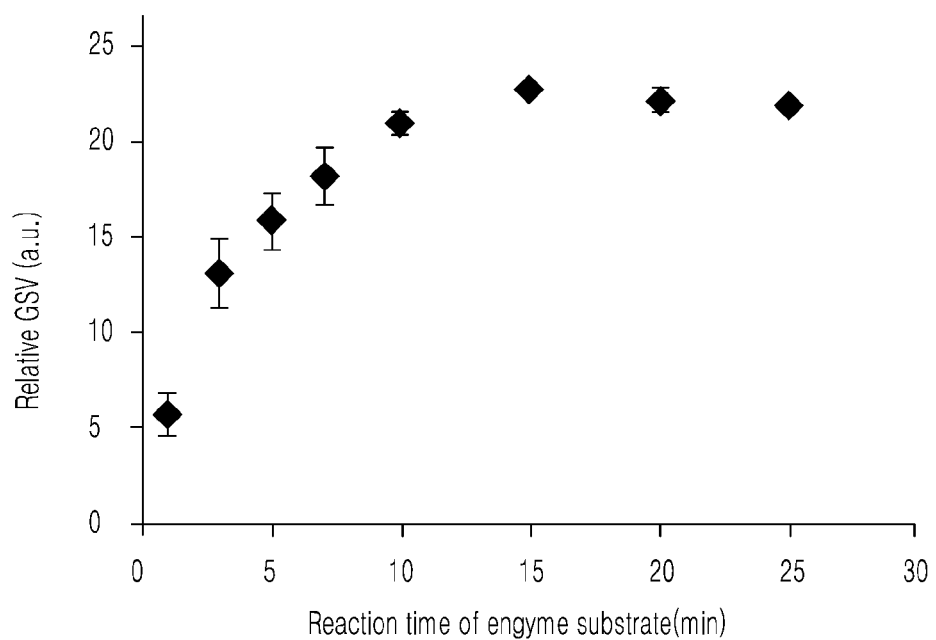
FIG. 10 is a graph showing the relationship between the amount of the added sample and the reaction time.

Meanwhile, the graph of FIG. 10 shows the reaction time of the enzyme substrate and the amount of the produced reactant with a series of points. As shown in FIG. 10, it can be seen that the amount of the produced reactant increases as the reaction time increases until a certain point but the amount of the produced reactant keeps constant even after a certain time passes. That is, it can be seen that the smaller the amount of sample or the like is, the shorter the required reaction time is as in the present invention.

Figure 11:
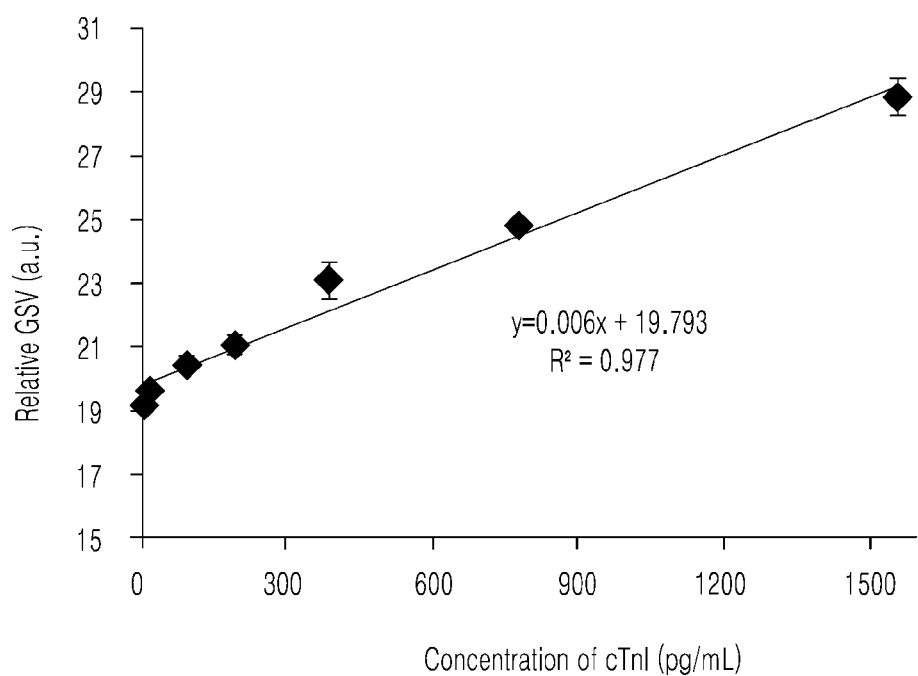
FIG. 11 is a graph showing the input sample amount and cTnI concentration for each of the pictures shown in FIG. 9.
Figure 12:
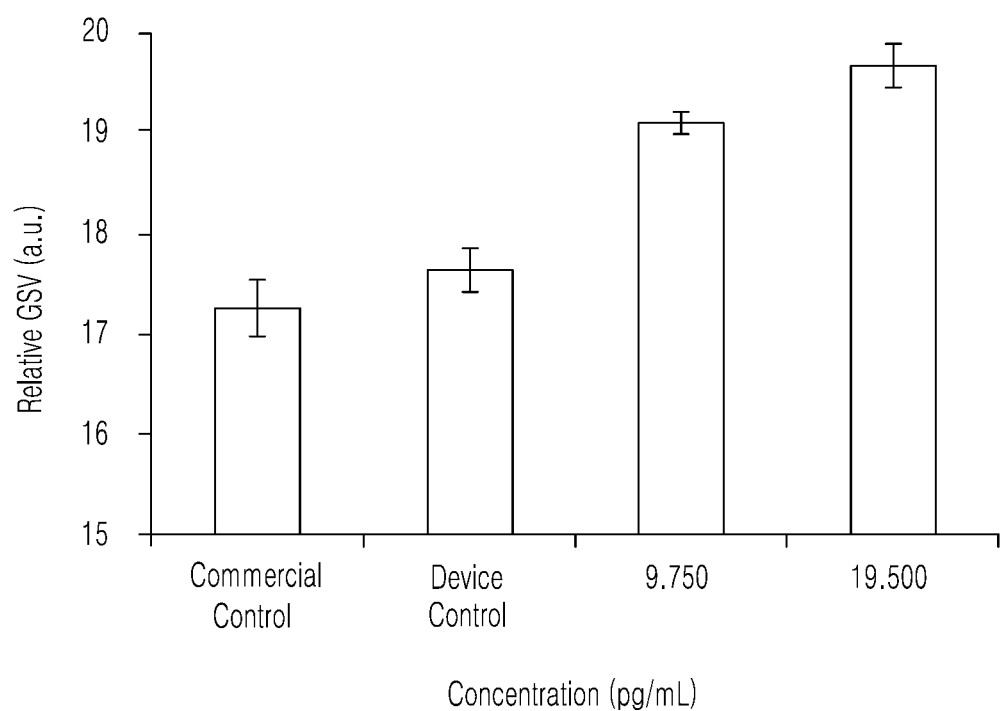
FIG. 12 is a graph showing the relationship between the amount and concentration of an injected sample.

The graphs shown in FIGS. 11 and 12 show the amount of the product according to the concentration of cTnI, and are graphs corresponding to the photographs shown in FIG. 9. It can be seen that the amount of the product has a linear relationship with the concentration of cTnI. However, since the concentration at which a clear reaction result can be obtained is 97.5 pg/mL as previously seen, there is no need to increase the concentration of cTnI more than that.

The table shown in FIG. 13 is a comparison of the amount of sample and the reaction time required in the ELISA reaction process using the conventional 96-well plate and in the ELISA reaction process using the microfluidic reaction device according to the present invention. The leftmost data is the amount and time required in the case of the present invention, and it can be seen that the amount of the sample and reaction time required in the present invention are significantly smaller than that of the prior art.

As described so far, in the present invention, owing to the reaction section formed with an extremely small height, the immunoreaction test is possible even with a small amount of sample, so that the required cost and time are drastically reduced. And, furthermore, due to the interaction between the suction pump and the pressure release sections, a plurality of channels can react independently and sequentially. In addition, it is automatically and conveniently performed without any preparatory procedures such as supplying reagents with a dropper every time for a series of reactions in one reaction zone and washing a microbeaker between reactions and reactions. Therefore, there is no need for the labor of performing an immunoreaction test with concentration for a long time, and the time required for the entire reaction process is further shortened.

Therefore, the examination apparatus according to the present invention can perform an examination on the spot even in an emergency situation requiring an urgent examination, thereby enabling a dramatic improvement in the quality of medical services.

The present invention described above is not limited by the above-described embodiments and the accompanying drawings but it will be obvious to those of ordinary skill in the art that various substitutions, modifications, and changes are possible within the scope of the technical spirit of the present invention.

The invention claimed is:

1. A microfluidic connection device comprising:
    a reaction plate comprising:
        a base plate;
        a reagent lifting column arranged on the base plate, through which reagents are lifted;
        a reaction zone located on an upper surface of the reagent lifting column;
        a supply tube and a discharge tube arranged inside the reagent lifting column so as to supply or discharge the reagents to or from the reaction zone; and
        a sealing cover sealing an upper portion of the reagent lifting column,
        wherein an observation window is formed in the sealing over to observe a chemical reaction between samples in the reaction zone, and immobilized capture antibodies are provided on an inner surface of the sealing cover.

2. The microfluidic connection device of claim 1, wherein the reaction plate has a plural set of the reagent lifting column, the reaction zone, the supply tube, the discharge tube and the sealing cover formed on the base plate,
    wherein the microfluidic connection device further comprises a plurality of microtubes, each of which is connected to corresponding one of the supply tubes so as to transfer a plurality of samples toward the reaction zone.

3. The microfluidic connection device of claim 2, further comprising:
    a microvalve for moving or stopping samples filled in the plurality of microtubes.

4. The microfluidic connection device of claim 3, wherein the microvalve comprises:
    a plate-shaped body in which the plurality of microtubes are embedded in parallel to each other;
    a plurality of bumpers formed in longitudinal direction on an upper surface of the plate-shaped body over an area where the plurality of microtubes are embedded; and
    a pressure roller bar provided on and across the plurality of bumpers for pressurizing the plurality of the bumpers by moving across the plurality of bumpers$_1$
    wherein the pressure roller bar or the plate-shaped body is configured to move in a longitudinal direction, and
    wherein the plate-shaped body and the plurality of bumpers are made out of elastic material, so that when either the pressure roller bar or the plate-shaped body is moved, the pressure roller bar rolls along the upper portions of the plurality of bumpers to press the plurality of bumpers, thereby transferring samples filled in the plurality of microtubes by movement of compression areas formed in the plurality of microtubes by pressing of the plurality of bumpers.

5. The microfluidic connection device of claim 4, further comprising:
    a suction pump connected to the discharge tubes, for taking in a plurality of samples filled in the plurality of microtubes toward the reaction zone.

6. The microfluidic connection device of claim 4,
    wherein the microvalve further comprises pressure release sections in which the plurality of bumpers are not formed over the area where the plurality of microtubes are embedded, and
    wherein when the pressure roller bar is on the pressure release sections, the plurality of microtubes are released from compression.

7. The microfluidic connection device of claim 5, wherein the reaction plate comprises one discharge hole, all of the discharge tubes are connected to the one discharge hole, and the suction pump is connected to the one discharge hole.

* * * * *